United States Patent [19]
D'Silva

[11] Patent Number: 4,578,402
[45] Date of Patent: Mar. 25, 1986

[54] PESTICIDAL ALPHA-CYANOBENZYL PHENYL BENZOYL UREA COMPOUNDS

[75] Inventor: Themistocles Damasceno J. D'Silva, Chapel Hill, N.C.

[73] Assignee: Union Carbide Corporation, Danbury, Conn.

[21] Appl. No.: 712,195

[22] Filed: Mar. 15, 1985

[51] Int. Cl.$^4$ ..................... A01N 37/34; C07C 121/78
[52] U.S. Cl. ................................... 514/521; 558/404; 514/522
[58] Field of Search .................. 260/465 D; 514/521, 514/522

[56] References Cited

U.S. PATENT DOCUMENTS 4,350,706  9/1982  Brouwer et al. ........... 260/465 D X

FOREIGN PATENT DOCUMENTS 895742   12/1982  Belgium .
031974   7/1981   European Pat. Off. .
116728   8/1984   European Pat. Off. .
116729   8/1984   European Pat. Off. .
54-012343 1/1979  Japan .
59-020265 2/1984  Japan .

OTHER PUBLICATIONS

R. B. Davis et al., *J. Amer. Chem. Soc.*, vol. 82, pp. 2913-2915 (1960).
R. B. Davis et al., *J. Org. Chem.*, vol. 26, pp. 4270-4274 (1961).
M. Makosza et al., *Tetrahedron*, vol. 30, pp. 3723-3735 (1974).

*Primary Examiner*—Dolph H. Torrence
*Attorney, Agent, or Firm*—Gerald L. Coon

[57] ABSTRACT

Novel alpha-cyanobenzyl phenyl benzoyl urea compounds are provided together with methods for their preparation and the use of said compounds as the active toxicant in pesticidal compositions.

35 Claims, No Drawings

PESTICIDAL ALPHA-CYANOBENZYL PHENYL BENZOYL UREA COMPOUNDS

BRIEF SUMMARY OF THE INVENTION

1. Technical Field

This invention relates to novel alpha-cyanobenzyl phenyl benzoyl urea compounds which are useful as the active toxicant in pesticidal compositions. This invention also relates to a method for the preparation of the novel alpha-cyanobenzyl phenyl benzoyl urea compounds. This invention further relates to pesticidal compositions and to a method for their use.

2. Background of the Invention

In recent years a variety of benzoyl urea compounds have been reported in the literature as having pesticidal activity. For example, benzyloxyphenylbenzoyl urea compounds and their use as insecticides and miticides have been disclosed in Japanese Patent Application No. 5 9020 265 published Feb. 1, 1984. Japanese Patent Application No. 5 4012 345 published Jan. 30, 1979, U.S. Pat. No. 4,350,706 issued Sept. 21, 1982 and European Patent Application Publication No. 116,728 published Aug. 29, 1984. Also, benzyloxymethylphenylbenzoyl urea compounds and phenyloxymethylphenylbenzoyl urea compounds and their use as insecticides and miticides have been disclosed in European Patent Application Publication No. 31974 published July 15, 1981.

Further, benzamide compounds have been reported in the literature as having anthelmintic properties. For example, Belgium Patent No. 895,742 issued May 16, 1983 disclosed the preparation of phenyl alpha-cyanomethyl anilines and their use as intermediates in the preparation of benzamide compounds having anthelmintic properties such as N-[5-chloro-4-[(4-chlorophenyl)cyanomethyl]-2-methylphenyl]-2-hydroxy-3,5-diiodo-benzamide.

Accordingly, one or more of the following objects will be achieved by the practice of this invention. It is an object of this invention to provide novel alpha-cyanobenzyl phenyl benzoyl urea compounds which exhibit outstanding pesticidal activity. Another object of this invention is to provide methods or processes for the preparation of the novel alpha-cyanobenzyl phenyl benzoyl urea compounds. A further object is to provide novel pesticidal compositions containing the novel alpha-cyanobenzyl phenyl benzoyl urea compounds as the active toxicant. A still further object of this invention is to provide a method for controlling pests by the application of the novel pesticidal compositions. These and other objects will readily become apparent to those skilled in the art in light of the teachings herein set forth.

DISCLOSURE OF THE INVENTION

This invention relates to novel alpha-cyanobenzyl phenyl benzoyl urea compounds, pesticidal compositions thereof, and a process for their preparation and use. The alpha-cyanobenzyl phenyl benzoyl urea compounds of this invention are those represented by the following generic formula:

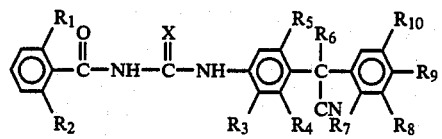

wherein: $R_1$, $R_2$, $R_3$, $R_4$, $R_5$, $R_6$, $R_7$, $R_8$, $R_9$, $R_{10}$ and X are as hereinafter described.

DETAILED DESCRIPTION

As indicated above, the novel alpha-cyanobenzyl phenyl benzoyl urea compounds of this invention are conveniently represented by the following formula:

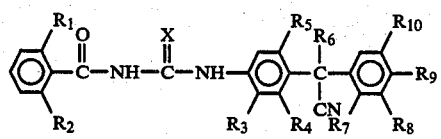

wherein:
$R_1$ and $R_2$ are independently hydrogen, halogen, $C_{1-6}$ alkyl, haloalkyl, polyhaloalkyl, alkoxy, haloalkoxy or polyhaloalkoxy, provided that at least one of $R_1$ and $R_2$ is other than hydrogen;

$R_3$, $R_4$ and $R_5$ are independently hydrogen, halogen, $C_{1-6}$ alkyl, haloalkyl, polyhaloalkyl, alkoxy, haloalkoxy, polyhaloalkoxy, carboxylic acid, carboxylic acid salt or carboxylic acid ester;

$R_6$ is hydrogen or $C_{1-4}$ alkyl;

$R_7$, $R_8$, $R_9$ and $R_{10}$ are independently hydrogen, halogen, $C_{1-6}$ alkyl, haloalkyl, polyhaloalkyl, alkoxy, haloalkoxy, polyhaloalkoxy, carboxylic acid, carboxylic acid salt, carboxylic acid ester, cyano or nitro; and X is oxygen or sulfur.

The novel compounds of this invention are illustrated by, but not limited to, the following:

1-[2,5-dichloro-4-(alpha-cyano-4-fluorobenzyl)phenyl]-3-(2,6-difluorobenzoyl)urea;

1-[2-methyl-5-chloro-4-(alpha-cyano-4-chlorobenzyl)phenyl]-3-(2,6-difluorobenzoyl)urea;

1-[2,5-dichloro-4-(alpha-cyano-4-chlorobenzyl)phenyl]-3-(2,6-difluorobenzoyl)urea;

1-[4-(alpha-cyano-4-methylbenzyl)phenyl]-3-(2,6-difluorobenzoyl)urea;

1-[2,5-dichloro-4-(alpha-cyano-2,4-dimethylbenzyl)phenyl]-3-(2,6-difluorobenzoyl)urea;

1-[2,5-dichloro-4-(alpha-cyano-4-fluorobenzyl)phenyl]-3-(2-fluorobenzoyl)urea;

1-[2-methyl-5-chloro-4-(alpha-cyano-alpha-methyl-4-chlorobenzyl)phenyl]-3-(2,6-difluorobenzoyl)urea;

1-[2,5-dichloro-4-(alpha-cyano-4-methylbenzyl)phenyl]-3-(2,6-difluorobenzoyl)thiourea;

1-[3-chloro-2,5-dimethyl-4-(alpha-cyano-4-chlorobenzyl)phenyl]-3-(2,6-difluorobenzoyl)urea;

1-[2,3,5-trichloro-4-(alpha-cyano-4-methylbenzyl)phenyl]-3-(2,6-difluorobenzoyl)urea;

1-[2,5-dichloro-4-(alpha-cyano-alpha-propyl-4-chlorobenzyl)phenyl]-3-(2-chlorobenzoyl)urea;

1-[2,5-dichloro-4-(alpha-cyano-4-chlorobenzyl)phenyl]-3-(2,6-dimethoxybenzoyl)urea;

1-[2-methyl-5-chloro-4-(alpha-cyano-4-chlorobenzyl)phenyl]-3-(2-trifluoromethylbenzoyl)urea;

1-[2,5-dichloro-4-(alpha-cyano-4-trifluoromethoxybenzyl)phenyl]-3-(2,6-difluorobenzoyl)urea;

1-[2,5-dichloro-4-(alpha-cyano-2-bromo-4-chlorobenzyl)phenyl]-3-(2,6-difluorobenzoyl)urea;
1-[2-methyl-5-chloro-4-(alpha-cyano-4-bromobenzyl)phenyl]-3-(2,6-difluorobenzoyl)urea;
1-[2,3-dichloro-4-(alpha-cyano-4-chlorobenzyl)phenyl]-3-(2-trifluoromethoxybenzoyl)urea;
1-[2-chloro-5-trifluoromethyl-4-(alpha-cyano-4-cyanobenzyl)phenyl]-3-(2,6-difluorobenzoyl)urea;
1-[2-chloro-5-ethoxycarbonyl-4-(alpha-cyano-2,4-dichlorobenzyl)phenyl]-3-(2,6-difluorobenzoyl)urea;
1-[2,5-dichloro-4-(alpha-cyano-2-bromo-4-methoxybenzyl)phenyl]-3-(2,6-difluorobenzoyl)urea.

The novel alpha-cyanobenzyl phenyl benzoyl urea compounds of this invention can be prepared by one or more methods. For example, the compounds of this invention can be prepared by reacting a substituted isocyanate or isothiocyanate (ii) with a benzamide (i) as follows:

SCHEME I

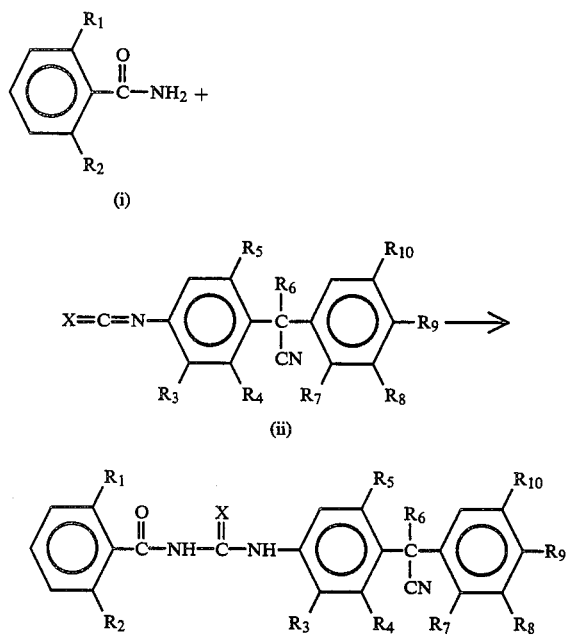

wherein $R_1$, $R_2$, $R_3$, $R_4$, $R_5$, $R_6$, $R_7$, $R_8$, $R_9$, $R_{10}$ and X are as hereinbefore described.

Alternatively, the novel compounds of this invention can be prepared by the reaction of a benzoyl halide (iii) with a substituted urea or thiourea (iv) as follows:

SCHEME II

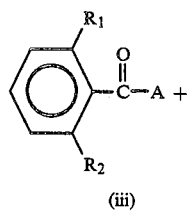

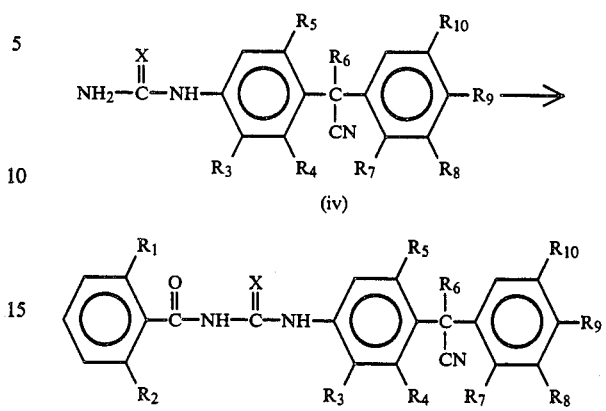

wherein A is halogen and $R_1$, $R_2$, $R_3$, $R_4$, $R_5$, $R_6$, $R_7$, $R_8$, $R_9$, $R_{10}$ and X are as hereinbefore described.

The novel compounds of this invention can also be prepared by reacting a substituted aniline (vi) with a benzoyl isocyanate or benzoyl isothiocyanate (v) as follows:

SCHEME III

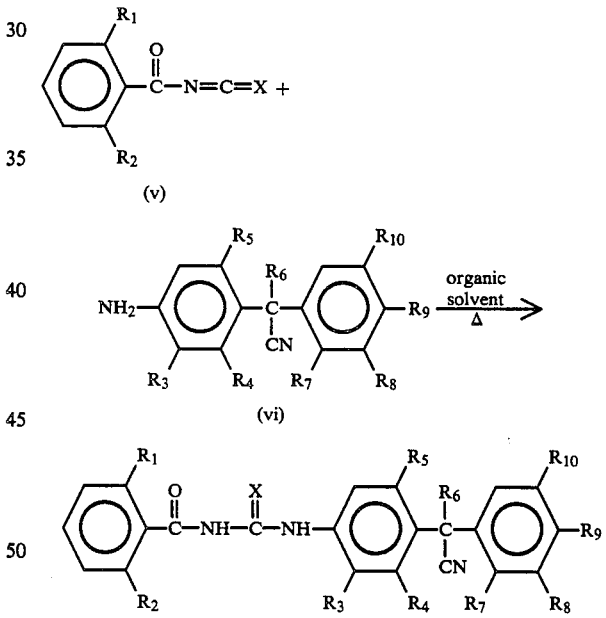

wherein $R_1$, $R_2$, $R_3$, $R_4$, $R_5$, $R_6$, $R_7$, $R_8$, $R_9$, $R_{10}$ and X are as hereinbefore described.

In general, the reactions illustrated in Schemes I, II and III can be carried out in organic solvents such as aromatic hydrocarbons, halogenated hydrocarbons or ethers. Solvents like toluene, 1,2-dichloroethane and p-dioxane are preferred. The reactions in general proceed at temperatures ranging from about ambient temperature to about 100° C.

The intermediates shown in Schemes I, II, and III can be prepared according to generally accepted procedures. Thus, the substituted benzoyl isocyanate (v) (X=O) can be prepared from the corresponding benzamide according to the general procedure of Speziale et. al., *J. Org. Chem.*, 27, 3762 (1962) as follows:

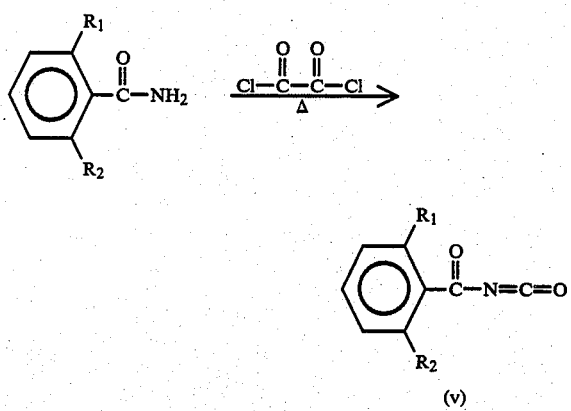

The substituted benzoyl isothiocyanate (v) (X=S) can be prepared by reacting a benzoyl chloride with potassium thiocyanate according to the procedure of Ambelang et. al. *J. Amer. Chem. Soc.* 61, 632 (1939) as follows:

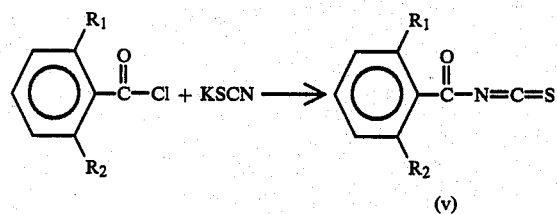

The aniline compounds of the type (vi) can be prepared as follows:

SCHEME IV

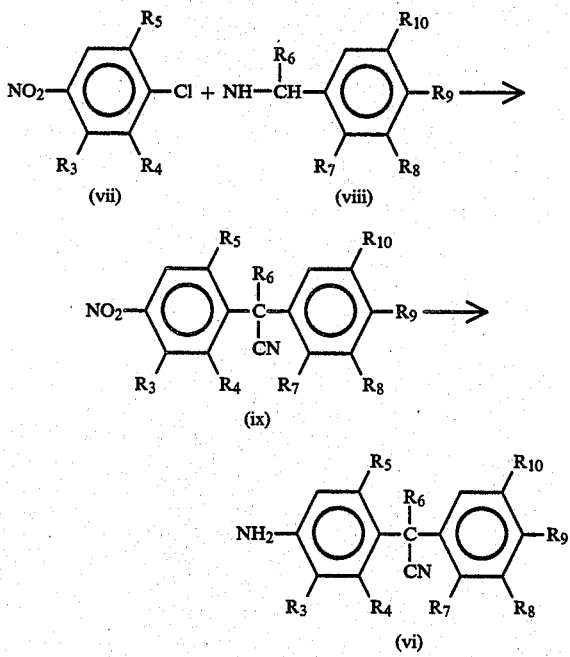

wherein $R_3$, $R_4$, $R_5$, $R_6$, $R_7$, $R_8$, $R_9$, $R_{10}$ and X are as hereinbefore described.

The aniline compounds of the type (vi) can also be prepared from an oxime such as a 4-(phenylcyanomethylene)-cyclohexa-2,5-diene-1-one oxime, the preparation of which is described by R. B. Davis, L. C. Pizzini and J. D. Benigni, The Condensation of Aromatic Nitro Compounds with Arylacetonitriles, *J. Amer. Chem. Soc.*, Vol. 82, pp. 2913–2915, (1960) and R. B. Davis, L. C. Pizzini and E. J. Bara, *J. Org. Chem.*, vol. 26, pp 4270–4274 (1961). See also Example 1 hereinafter.

The compounds of the type (ix) can be prepared in accordance with the procedure described by M. Makosza, M. Jagusztyn-Grochowska and M. Ludwikow, Reactions of Phenylacetonitirle Derivatives with Aromatic Nitrocompounds in Basic Media, *Tetrahedron*, Vol. 30, pp. 3723–3735 (1974).

The reaction of compound (viii) with chloronitrobenzene (vii) to give compound (ix) proceeds in the presence of a base in an inert solvent at elevated temperature. The bases suitable for this reaction are potassium carbonate, sodium hydride, potassium hydroxide and sodium hydroxide. Suitable solvents are acetone, toluene, dimethylformamide, and dimethylsulfoxide. The above reaction can also be achieved biphasely in the presence of a phase-transfer catalyst.

The reduction of compound (ix) to aniline (vi) can be achieved by hydrogenation using a catalytic amount of platinum or palladium on carbon under pressure, ranging from 20–100 psi at ambient temperature. Suitable solvents for hydrogenation include aromatic hydrocarbons or alcohols. The reduction can also be achieved by a chemical method using the procedure described in United Kingdom Patent No. 1,456,964 to E. Endus et al..

Isocyanate or isothiocyanate (ii) can be obtained by reacting the substituted aniline (vi) with phosgene or thiophosgene. Urea or thiourea (iv) can be obtained by the treatment of (ii) with ammonium hydroxide. These procedures are depicted as follows:

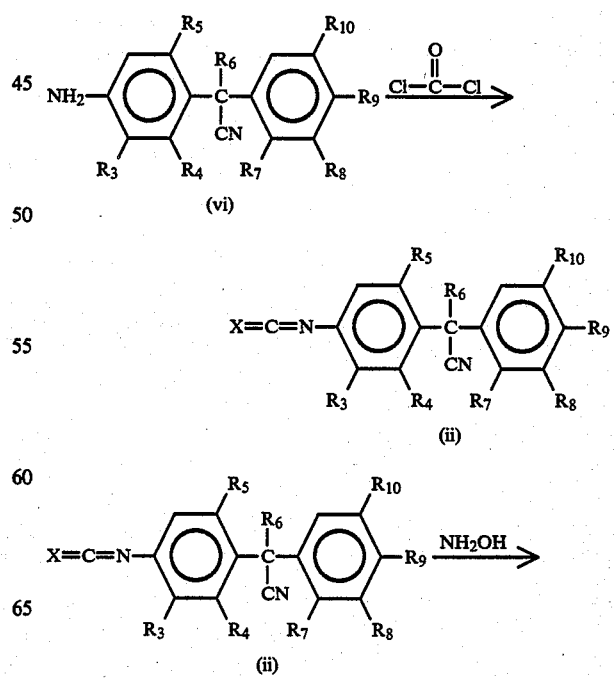

-continued $$H_2N-\overset{X}{\underset{\|}{C}}-NH-\underset{R_3}{\underset{|}{\bigcirc}}\underset{R_4}{\overset{R_5}{|}}-\overset{R_6}{\underset{CN}{\overset{|}{C}}}-\underset{R_7}{\underset{|}{\bigcirc}}\underset{R_8}{\overset{R_{10}}{|}}-R_9$$

(iv)

wherein $R_3$, $R_4$, $R_5$, $R_6$, $R_7$, $R_8$, $R_9$, $R_{10}$ and X are as hereinbefore described.

Benzamide (i) and benzoyl halide (iii) are available commercially or can be prepared by conventional methods known in the art.

Other intermediates which are useful in the preparation of the novel compounds of this invention can be prepared by known methods.

2-Nitro-4,5-dichlorotoluene can be obtained by the reaction of 3,4-dichlorotoluene using 90% nitric acid as follows:

Another intermediate 2,5-dimethyl-3,4-dichloronitrobenzene can be obtained by the reactions as follows:

The compounds contemplated in this invention may be applied as pesticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, dimethylformamide or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentration will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the pests, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

Mixtures of the active compounds may be employed if desired as well as combinations of the active compounds of this invention with other biologically active compounds or synergists.

The following examples are illustrative of methods utilized in the preparation of compounds of this invention.

EXAMPLE 1

Part A: Preparation of 4-(alpha-cyano-4-fluorobenzylidine)-2,5-dichlorocyclohexa-2,5-diene-1-one oxime Into a 300 milliliter reaction flask equipped with a magnetic stirrer and nitrogen inlet and outlet was added a solution of 16.8 grams (0.3 moles) of potassium hydroxide in 150 milliliters of methanol, 19.2 grams (0.1 moles) of 2,5-dichloronitrobenzene and 13.5 grams (0.1 moles) of 4-fluorobenzylcyanide under a nitrogen atmosphere at ambient temperature. The reaction mixture immediately turned to a dark brown color and, within 15 minutes, turned into a paste. The paste was diluted with 250 milliliters of water and concentrated hydrochloric acid was added to give a yellow precipitate. The yellow precipitate was filtered, dried overnight in a vacuum oven at 50° C. and stirred into ethyl acetate. Recrystallization from ethyl acetate afforded 19.6 grams of a yellow solid having a melting point of 173°-175° C. Elemental analysis of the yellow solid indicated the following:

Analysis: $C_{14}H_7Cl_2FN_2O\cdot H_2O$: Calculated: C, 51.4; H, 2.15; N, 8.56. Found: C, 52.5; H, 2.19; N, 8.67.

Part B: Preparation of 2,5-dichloro-4-(alpha-cyano-4-fluorobenzyl)aniline

Into a 500 milliliter found bottom flask equipped with a thermometer, magnetic stirrer, nitrogen inlet and outlet and condenser was added a solution of 16 milliliters of methanol in 120 milliliters of water, 8.0 grams (0.025 moles) of 4-(alpha-cyano-4-fluorobenzylidine)-2,5-dichlorocyclohexa-2,5-diene-1-one oxime prepared in Part A and 6.0 grams of sodium hydrosulfide under a nitrogen atmosphere at ambient temperature. The reaction mixture was then heated in an oil bath under reflux conditions for a period of 2 hours. After cooling to ambient temperature, the reaction mixture was extracted in ethyl acetate, dried over sodium sulfate and concentrated to give 5.4 grams of a solid having a melting point of 95° C.-98° C. Elemental analysis of the solid indicated the following:

Analysis: $C_{14}H_9Cl_2FN_2$; Calculated: C, 56.97; H, 3.07; N, 9.49; F, 6.43; Cl, 24.03. Found: C, 56.10; H, 3.15; N, 9.14; F, 6.28; Cl 23.66.

Part C: Preparation of 1-[2,5-dichloro-4-(alpha-cyano-4-fluorobenzyl)phenyl]-3-(2,6-difluorobenzoyl)urea Into a 100 milliliter round bottom flask equipped with a thermometer, magnetic stirrer and condenser was added 30 milliliters of toluene, 1.2 grams (0.004 moles) of 2,5-dichloro-4-(alpha-cyano-4-fluorobenzyl)aniline prepared in Part B and 1.0 grams (0.005 moles) of 2,6-difluorobenzoyl isocyanate under a nitrogen atmosphere at ambient temperature. The reaction mixture was then heated in an oil bath for a period of 2 hours. After cooling to ambient temperature, the reaction mixture was filtered and dried overnight in a vacuum oven at 50° C. This afforded 1.3 grams of a white solid having a melting point of 216° C.-218° C. Elemental analysis of the white solid indicated the following:

Analysis: $C_{22}H_{12}Cl_2F_3N_3O_2$; Calculated: C, 55.25; H, 2.53; N, 8.79; Cl, 14.82; F, 11.91. Found: C, 55.19; H, 2.51; N, 8,58; Cl, 15.20; F, 12.15.

EXAMPLES 2 THROUGH 17

In a manner similar to that employed in Example 1, and utilizing one of the synthesis schemes previously disclosed, other alpha-cyanobenzyl phenyl benzoyl urea compounds were prepared. The identity of the substituents on the generic formula and the analytical data are set forth in Table I below.

TABLE 1
Alpha-Cyanobenzyl Phenyl Benzoyl Urea Compounds

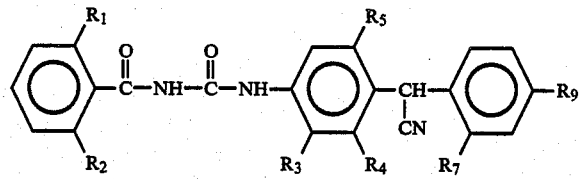

| Example | Molecular Formula | $R_1$ | $R_2$ | $R_3$ | $R_4$ | $R_5$ | $R_7$ | $R_9$ | Calculated C | Calculated H | Calculated N | Found C | Found H | Found N | Melting Point °C. |
|---|---|---|---|---|---|---|---|---|---|---|---|---|---|---|---|
| 2 | $C_{23}H_{15}Cl_2F_2N_3O_2$ | F | F | $CH_3$ | H | Cl | H | Cl | 58.25 | 3.18 | 8.86 | 58.65 | 3.30 | 8.69 | 235–238 |
| 3 | $C_{22}H_{12}Cl_3F_2N_3O_2$ | F | F | Cl | H | Cl | H | Cl | 53.41 | 2.44 | 8.49 | 54.54 | 2.87 | 7.82 | 230–233 |
| 4 | $C_{24}H_{17}Cl_2F_2N_3O_2$ | F | F | Cl | H | Cl | $CH_3$ | $CH_3$ | 58.97 | 3.51 | 8.60 | 59.11 | 3.68 | 8.38 | 188–190 |
| 5 | $C_{22}H_{11}Cl_4F_2N_3O_2$ | F | F | Cl | H | Cl | Cl | Cl | 49.90 | 2.09 | 7.95 | 48.00 | 2.23 | 7.16 | 198–201 |
| 6 | $C_{23}H_{15}ClF_3N_3O_3$ | F | F | $OCH_3$ | H | F | H | Cl | 58.30 | 3.19 | 8.86 | 58.66 | 3.30 | 8.61 | 243–245 |
| 7 | $C_{22}H_{13}Cl_3FN_3O_2$ | H | Cl | Cl | H | Cl | H | F | 55.42 | 2.75 | 8.81 | 55.40 | 3.00 | 8.29 | 145–149 |
| 8 | $C_{22}H_{13}Cl_4N_3O_2$ | H | Cl | Cl | H | Cl | H | Cl | 53.58 | 2.65 | 8.52 | 53.60 | 2.88 | 8.36 | 189–192 |
| 9 | $C_{22}H_{12}Cl_4FN_3O_2$ | Cl | Cl | Cl | H | Cl | H | F | 51.68 | 2.37 | 8.21 | 51.70 | 2.65 | 7.80 | 171–173 |
| 10 | $C_{22}H_{15}F_2N_3O_2$ | F | F | H | H | H | H | H | 67.51 | 3.86 | 10.74 | 67.03 | 4.06 | 10.59 | 198–201 |
| 11 | $C_{23}H_{17}F_2N_3O_2$ | F | F | H | H | H | H | $CH_3$ | — | — | — | — | — | — | 221–223 |
| 12 | $C_{22}H_{13}Cl_2F_2N_3O_2$ | F | F | Cl | Cl | H | H | H | 57.40 | 2.85 | 9.13 | 57.83 | 2.90 | 8.85 | 217–219 |
| 13 | $C_{24}H_{19}ClFN_3O_2$ | F | F | $CH_3$ | H | Cl | $CH_3$ | H | 63.50 | 3.99 | 9.26 | 63.70 | 4.17 | 9.05 | 222–224 |
| 14 | $C_{23}H_{15}Cl_2F_2N_3O_2$ | F | F | H | Cl | Cl | $CH_3$ | H | — | — | — | — | — | — | 208–211 |
| 15 | $C_{23}H_{15}Cl_2F_2N_3O_2$ | F | F | Cl | Cl | H | $CH_3$ | H | 58.24 | 3.18 | 8.85 | 57.78 | 3.13 | 8.73 | 210–212 |
| 16 | $C_{22}H_{13}Cl_2F_2N_3O_2$ | H | F | Cl | H | Cl | H | H | — | — | — | — | — | — | 202–203 |
| 17 | $C_{22}H_{12}Cl_3F_2N_3O_2$ | F | F | Cl | Cl | H | H | Cl | — | — | — | — | — | — | 244–245 |

Certain representative examples of the novel compounds of this invention were evaluated to determine their pesticidal activity against certain insects, including a caterpillar and a beetle.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. Certain of the test compounds were also prepared by dissolving 375 mg of compound in 7.5 ml of dimethylformamide. Fifteen milliliters of acetone containing 37.5 mg (10 percent of the weight of test compound) of an alkylphenoxy polyethoxyethanol surfactant, as a wetting-/emulsifying/dispersing agent was added to the dimethylformamide solution. Fifty-two and one-half milliliters of water was mixed into the dimethylformamide-acetone mixture to give roughly 75 ml of a suspension containing the compound in solution or in finely divided form. The thus prepared stock suspension contained 0.5 percent by weight of compound. The test procedures were as follows:

Southern Armyworm Leaf Spray Bait Test

Larvae of the southern armyworm (Spodoptera eridania, (Cram.), reared on Tendergreen bean plants at a temperature of 80°±5° F. and a relative humidity of 50±50 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound was also sprayed on infested plants. When dry, the paired leaves were separated and each one was placed in a 9 centimeter Petri dish lined with moistened filter paper. Five randomly selected larvae were introduced into each dish and the dishes were closed. The closed dishes were lableled and held at 80°-85° F. for up to five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (Epilachna varivestic, Muls.), reared on Tendergreen bean plants at a temperature of 80°±5° F. and 50±5 percent relative humidity, were the test insects. For certain of the tests second instar larvae (weighting about 6 mg) of the Mexican bean beetle (*Epilachna varivestis*, Muls.), reared on Sieva Pole lima bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound was also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead. Percent mortality was recorded for various concentration levels.

Tobacco Budworm and Cotton Bollworm Leaf Spray Bait Test

Second instar larvae of the tobacco budworm (weighing about 4.5 mg) (*Heliothis virescens*, F.) and the cotton bollworm (weighing about 2.5 mg) (*Heliothis zea*, (Boddie)), obtained commercially and reared on artificial diet at a temperature of 80° C.±5° F. and a relative humidty of 50±5 percent, constituted the test insects.

Using a procedure similar to the above, but substituting cotton plants for snapbeans, treated and dried cotton leaves were introduced into 9 cm Petri dishes which were organized into groups of 10-dish sets. One randomly selected larvae was introduced into each dish of a ten dish set and the dishes were closed. The closed dishes were labelled and held at 80°±5° F. for five days. Larvae which were unable to move the length of the body, even upon stimulation, were considered dead. Percent mortality was recorded for various concentration levels. $LC_{50}$ or concentration required to kill 50 percent of the larvae was determined from the mortality figures.

The biological properties of certain representative examples of the compounds of this invention are set forth in Tables II and III below. The compound of Example A in Table II is included for comparison purposes.

TABLE II

Biological Properties of Representative Alpha-Cyanobenzyl Phenyl Benzoyl Urea Compounds

| Compound Prepared in Example No. | Activity at 500 ppm[3] | |
|---|---|---|
| | SAW[1] | MBB[2] |
| 1 | A | A |
| 2 | A | A |
| 3 | A | A |
| 4 | A | B |
| 5 | A | A |
| 6 | A | A |
| 7 | A | A |
| 8 | A | A |
| 9 | A | A |
| 10* | C | C |
| 11 | A | A |
| 12 | A | B |
| 13 | A | A |
| 14 | A | A |
| 15 | A | A |
| A[4] | C | C |

[1] Southern Armyworm
[2] Mexican Bean Beetle
[3] Code:
A = 71-100% Kill
B = 31-70% Kill
C = 0-30% Kill
[4] N—[2,5-dichloro-4-(4-chlorophenylcyanomethylene)phenyl]-2,6-difluorobenzamide prepared in a manner similar to the procedure described in Belgium Patent 895,742.
*Tested at 100 ppm.

TABLE II

Biological Properties of Representative Alpha-Cyanobenzyl Phenyl Benzoyl Urea Compounds

| Compound Prepared in Example No. | $LC_{50}$ Values in ppm | |
|---|---|---|
| | Heliothis Zea | Heliothis Virescens |
| 1 | 1.1 | 7.0 |
| 2 | — | 3.0 |
| 3 | 4.0 | 2.5 |
| 4 | — | >500 |

TABLE II-continued

Biological Properties of Representative
Alpha-Cyanobenzyl Phenyl Benzoyl
Urea Compounds

| Compound Prepared in Example No. | LC$_{50}$ Values in ppm | |
|---|---|---|
| | Heliothis Zea | Heliothis Virescens |
| 5 | — | 15 |

Although the invention has been illustrated by the preceding examples, it is not to be construed as being limited to the materials employed therein; but rather, the invention encompasses the generic area as hereinbefore disclosed. Various modifications and embodiments can be made without departing from the spirit and scope thereof.

I claim:

1. A compound of the formula:

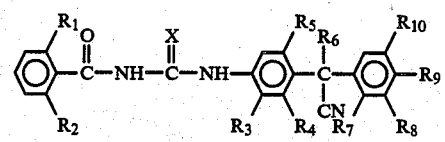

wherein:
R$_1$ and R$_2$ are independently hydrogen, halogen, C$_{1-6}$ alkyl, haloalkyl, polyhaloalkyl, alkoxy, haloalkoxy or polyhaloalkoxy, provided that at least one of R$_1$ and R$_2$ is other than hydrogen;
R$_3$, R$_4$ and R$_5$ are independently hydrogen, halogen, C$_{1-6}$ alkyl, haloalkyl, polyhaloalkyl, alkoxy, haloalkoxy, polyhaloalkoxy, carboxylic acid, carboxylic acid salt or carboxylic acid ester;
R$_6$ is hydrogen or C$_{1-6}$ alkyl;
R$_7$, R$_8$, R$_9$ and R$_{10}$ are independently hydrogen, halogen, C$_{1-6}$ alkyl, haloalkyl, polyhaloalkyl, alkoxy, haloalkoxy, polyhaloalkoxy, carboxylic acid, carboxylic acid salt, carboxylic acid ester, cyano or nitro; and
X is oxygen or sulfur.

2. The compound of claim 1 wherein at least one of R$_3$, R$_4$ and R$_5$ is other than hydrogen.

3. The compound of claim 1 wherein at least one of R$_7$, R$_8$, R$_9$ and R$_{10}$ is other than hydrogen.

4. The compound of claim 1 wherein at least one of R$_3$, R$_4$ and R$_5$ is other than hydrogen and at least one of R$_7$, R$_8$, R$_9$ and R$_{10}$ is other than hydrogen.

5. The compound of claim 1 wherein R$_1$ and R$_2$ are other than hydrogen.

6. The compound of claim 1 wherein at least two of R$_3$, R$_4$ and R$_5$ are other than hydrogen.

7. The compound of claim 1 wherein at least two of R$_7$, R$_8$, R$_9$ and R$_{10}$ are other than hydrogen.

8. The compound of claim 1 wherein R$_1$ and R$_2$ are other than hydrogen and at least two of R$_3$, R$_4$ and R$_5$ are other than hydrogen.

9. The compound of claim 1 wherein R$_1$ and R$_2$ are other than hydrogen and at least one of R$_7$, R$_8$, R$_9$ and R$_{10}$ is other than hydrogen.

10. The compound of claim 1 wherein R$_1$ and R$_2$ are other than hydrogen, at least two of R$_3$, R$_4$ and R$_5$ are other than hydrogen and at least one of R$_7$, R$_8$, R$_9$ and R$_{10}$ is other than hydrogen.

11. The compound of claim 1 which is 1-[2,5-dichloro-4-(alpha-cyano-4-fluorobenzyl)phenyl]-3-(2,6-difluorobenzoyl)urea.

12. The compound of claim 1 which is 1-[2-methyl-5-chloro-4-(alpha-cyano-4-chlorobenzyl)phenyl]-3-(2,6-difluorobenzoyl)urea.

13. The compound of claim 1 which is 1-[2,5-dichloro-4-(alpha-cyano-4-chlorobenzyl)phenyl]-3-(2,6-difluorobenzoyl)urea.

14. The compound of claim 1 which is 1-[4-(alpha-cyano-4-methylbenzyl)phenyl]-3-(2,6-difluorobenzoyl)urea.

15. A pesticide composition comprising an an acceptable carrier and a pesticidally effective amount of the compound of claim 1.

16. A pesticide composition comprising an an acceptable carrier and a pesticidally effective amount of the compound of claim 2.

17. A pesticide composition comprising an an acceptable carrier and a pesticidally effective amount of the compound of claim 3.

18. A pesticide composition comprising an an acceptable carrier and a pesticidally effective amount of the compound of claim 4.

19. A pesticide composition comprising an an acceptable carrier and a pesticidally effective amount of the compound of claim 5.

20. A pesticide composition comprising an an acceptable carrier and a pesticidally effective amount of the compound of claim 6.

21. A pesticide composition comprising an an acceptable carrier and a pesticidally effective amount of the compound of claim 7.

22. A pesticide composition comprising an an acceptable carrier and a pesticidally effective amount of the compound of claim 8.

23. A pesticide composition comprising an an acceptable carrier and a pesticidally effective amount of the compound of claim 9.

24. A pesticide composition comprising an an acceptable carrier and a pesticidally effective amount of the compound of claim 10.

25. A method of controlling pests which comprises subjecting said pests to a pesticidally effective amount of the compound of claim 1.

26. A method of controlling pests which comprises subjecting said pests to a pesticidally effective amount of the compound of claim 2.

27. A method of controlling pests which comprises subjecting said pests to a pesticidally effective amount of the compound of claim 3.

28. A method of controlling pests which comprises subjecting said pests to a pesticidally effective amount of the compound of claim 4.

29. A method of controlling pests which comprises subjecting said pests to a pesticidally effective amount of the compound of claim 5.

30. A method of controlling pests which comprises subjecting said pests to a pesticidally effective amount of the compound of claim 6.

31. A method of controlling pests which comprises subjecting said pests to a pesticidally effective amount of the compound of claim 7.

32. A method of controlling pests which comprises subjecting said pests to a pesticidally effective amount of the compound of claim 8.

33. A method of controlling pests which comprises subjecting said pests to a pesticidally effective amount of the compound of claim 9.

34. A method of controlling pests which comprises subjecting said pests to a pesticidally effective amount of the compound of claim 10.

35. A process for the preparation of a compound of the formula:

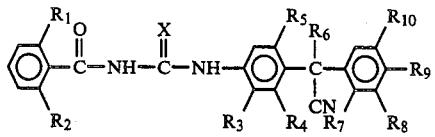

which comprises reacting an aniline of the formula:

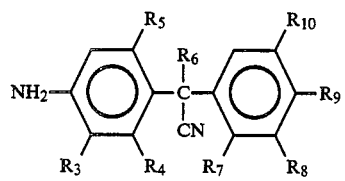

with a benzoyl isocyanate of the formula:

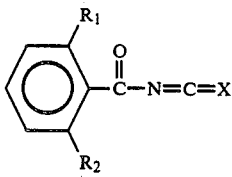

wherein:
$R_1$ and $R_2$ are independently hydrogen, halogen, $C_{1-6}$ alkyl, haloalkyl, polyhaloalkyl, alkoxy, haloalkoxy or polyhaloalkoxy, provided that at least one of $R_1$ and $R_2$ is other than hydrogen;
$R_3$, $R_4$ and $R_5$ are independently hydrogen, halogen, $C_{1-6}$ alkyl, haloalkyl, polyhaloalkyl, alkoxy, haloalkoxy, polyhaloalkoxy, carboxylic acid, carboxylic acid salt or carboxylic acid ester;
$R_6$ is hydrogen or $C_{1-4}$ alkyl;
$R_7$, $R_8$, $R_9$ and $R_{10}$ are independently hydrogen, halogen, $C_{1-6}$ alkyl, haloalkyl, polyhaloalkyl, alkoxy, haloalkoxy, polyhaloalkoxy, carboxylic acid, carboxylic acid salt, carboxylic acid ester, cyano or nitro; and
X is oxygen or sulfur.

* * * * *